(12) United States Patent
Jiang et al.

(10) Patent No.: US 10,894,254 B2
(45) Date of Patent: Jan. 19, 2021

(54) PORTABLE PATHOGEN ANALYSIS SYSTEM FOR DETECTING WATERBORNE PATHOGENS

(71) Applicants: The Regents of the University of California, Oakland, CA (US); California Institute of Technology, Pasadena, CA (US)

(72) Inventors: Sunny Jiang, Irvine, CA (US); Hamsa Gowda, Irvine, CA (US); Xiao Huang, Pasadena, CA (US); Xunyi Wu, Pasadena, CA (US); Marc Madou, Irvine, CA (US); Michael R. Hoffmann, Pasadena, CA (US)

(73) Assignees: THE REGENTS OF THE UNIVERSITY OF CALIFORNIA, Oakland, CA (US); CALIFORNIA INSTITUTE OF TECHNOLOGY, Pasadena, CA (US)

( * ) Notice: Subject to any disclaimer, the term of this patent is extended or adjusted under 35 U.S.C. 154(b) by 55 days.

(21) Appl. No.: 16/153,423

(22) Filed: Oct. 5, 2018

(65) Prior Publication Data
US 2019/0105653 A1    Apr. 11, 2019

Related U.S. Application Data

(60) Provisional application No. 62/568,423, filed on Oct. 5, 2017.

(51) Int. Cl.
*B01L 3/00*    (2006.01)
*B01L 7/00*    (2006.01)
(Continued)

(52) U.S. Cl.
CPC ... *B01L 3/502715* (2013.01); *B01L 3/502738* (2013.01); *B01L 3/502784* (2013.01);
(Continued)

(58) Field of Classification Search
CPC ..... B01L 3/502715; C12M 1/00; C12Q 1/701
See application file for complete search history.

(56) References Cited

U.S. PATENT DOCUMENTS 7,579,172 B2 *  8/2009  Cho ................... B01F 13/0071
                                                          435/91.2
8,303,911 B2 * 11/2012  Siegrist ................ B01L 3/5027
                                                          422/506

(Continued)

OTHER PUBLICATIONS

Mahony et al, Development of a Sensitive Loop-Mediated Isothermal Amplification Assay That Provides Specimen-to-Result Diagnosis of Respiratory Syncytial Virus Infection in 30 Minutes, 2013, Journal of Clinical Microbiology, 51, 2696-2701. (Year: 2013).*

(Continued)

*Primary Examiner* — Narayan K Bhat
(74) *Attorney, Agent, or Firm* — Nguyen Tarbet LLC

(57) ABSTRACT

A portable pathogen analysis system (PPAS) designed to detect microbial pathogens at the point-of-sample collection. The system comprises a concentration tube used for the concentration of microbes in large volumes of water samples using super absorbent polymer (SAP) beads and a hand-powered centrifuge; and a processing component, which functions as a portable lab-on-a-disc droplet digital nucleic acid amplification system, which integrates DNA extraction, nucleic acid amplification, and post-amplicon analysis in a single unit. The present invention provides a fast, cost-effective, and user-friendly solution for microbial water quality analysis in low-resource settings.

20 Claims, 1 Drawing Sheet
(1 of 1 Drawing Sheet(s) Filed in Color)

(51) Int. Cl.
*C12Q 1/6888* (2018.01)
*C12Q 1/70* (2006.01)

(52) U.S. Cl.
CPC ......... *B01L 7/00* (2013.01); *B01L 2200/0673* (2013.01); *B01L 2300/0627* (2013.01); *B01L 2300/0803* (2013.01); *B01L 2300/0867* (2013.01); *B01L 2300/18* (2013.01); *B01L 2400/0409* (2013.01); *B01L 2400/0688* (2013.01); *C12Q 1/6888* (2013.01); *C12Q 1/701* (2013.01)

(56) References Cited

U.S. PATENT DOCUMENTS

2009/0035847 A1* 2/2009 Cho .................... B01F 15/0233
435/289.1
2010/0081213 A1* 4/2010 Lee ........................ G01N 21/07
436/506
2016/0289729 A1* 10/2016 Richards ................. G02B 7/28

OTHER PUBLICATIONS

Saeed et al, Real-Time Polymerase Chain Reaction: Applications in Diagnostic Microbiology, 2013, 1, 28-36. (Year: 2013).*
Xie et al, Nanofiltration enabled by super absorbent polymer beads for concentrating microorganisms in water samples, 2016, Sci. Rep. 6, 20516;pp. 1-8, published Feb. 15, 2016. (Year: 2016).*
Siegrist et al, Serial siphon valving for centrifugal microfluidic platforms, 2010, Microfluid Nanofluid, 9:55-63 (Year: 2010).*
Huang, X et al. Portable Pathogen Analysis System (PPAS) for Microbial Water Quality Analysis. Submitted to the 21st International Conference on Miniaturized Systems for Chemistry and Life Sciences (MicroTAS 2017), 2017.

* cited by examiner

PORTABLE PATHOGEN ANALYSIS SYSTEM FOR DETECTING WATERBORNE PATHOGENS

CROSS REFERENCE

This application claims priority to U.S. Provisional Patent Application No. 62/568,423 filed Oct. 5, 2017, the specification(s) of which is/are incorporated herein in their entirety by reference.

FIELD OF THE INVENTION

The present invention relates to methods and systems for detecting pathogens in liquid samples, more particularly to portable systems for detecting pathogens in liquid samples.

BACKGROUND OF THE INVENTION

Waterborne diseases cause millions of death in developing countries or countries in conflict due to poor water and sanitation conditions. The detection and monitoring of waterborne pathogens is a critical step for the selection of water treatment processes that will lead to the control of disease transmission. The dPCR technique improves the accuracy and sensitivity of pathogen detection and it effectively reduces the analytical time from days to hours. However, most commercially available dPCR systems are designed for centralized laboratories that require trained personnel to operate. This requirement limits the routine application of dPCR in low-resource settings.

Microfluidic technologies have enabled the miniaturization of PCR analysis on chip-based devices that could potentially reduce costs, improve portability and allow for automatic control. One inherent drawback of microfluidic devices is the low sample volume processing ability. In comparison to clinical samples, the concentrations of pathogens in environmental water samples are often orders of magnitude lower.

The present invention features a portable pathogen analysis system (PPAS) for microbial water quality analysis at the point-of-sample collection. The system of the present invention is a digital nucleic acid amplification test system based on a Lab-on-a-Disc platform. Without wishing to limit the present invention to any theory or mechanism, it is believed that the system of the present invention is advantageous because it is fully automated by integrating DNA extraction, DNA amplification, and amplicon analysis in a single unit. The system can detect various microbial indicators and pathogens. The hands-on time may be less than a few minutes, and quantitative results may be obtained within an hour or two. Further, the system can be customized for detecting various microbial targets or other genetic markers by using different primers.

The present invention may be used for a variety of applications, including but not limited to microbial water quality analysis, disease identification at point-of-care, antibiotic susceptibility testing, food safety testing, agricultural quarantine inspections, and bioterrorism detection. For example, the system as presented herein is designed for water quality indicator microorganisms (e.g., *E. coli* and *Enterococcus* and MS2 phage) as well as waterborne microbial pathogens detection and quantification in low-resource settings. In some embodiments, the system can accommodate blood, feces and urine samples, which would make it useful for disease identification at point-of-care. The system may be modified to offer high throughput, highly parallel, and single-cell level antibiotic susceptibility testing. In some embodiments, the system can be used for detecting pathogens and spoilage organisms in food or food samples. Further, by adding an air filter, the system may be able to be developed into an airborne pathogen detection system, which could be very useful for early detection and rapid response to bioterrorism. In some embodiments, the system is modified to accommodate seawater.

SUMMARY OF THE INVENTION

The present invention features a portable pathogen analysis system (PPAS) for assessing water quality by detecting pathogens. The stand-alone system of the present invention facilitates microbial water quality analysis at the point-of-sample collection, particularly in a resource-limited setting. The system of the present invention comprises a concentration tube (see FIG. 1) designed for concentrating the pathogen without using electricity, and a processing component, a sample-in-answer-out platform that features a disposable microfluidic disc (see FIG. 2) and a portable analysis device (see FIG. 3), e.g., a rotation based thermal cycler. The flow of sample and reagents on the microfluidic disc is controlled by different rotation speeds and various passive valves.

The use of the system only requires one step wherein the sample is loaded into the system. The final quantitative results can be acquired within a few hours, e.g., 1-2 hours, 1-3 hours, 2-4 hours, etc.

Briefly, beads (e.g., superabsorbent polymer (SAP) beads) are packed into centrifuge tubes above a mesh holder. Due to size exclusion and charge repulsion, the beads only absorb water via osmosis, while the target microorganisms are excluded and remain in the concentrate after low-speed hand-powered centrifugation (see FIG. 1). The concentrated water samples are then processed using the processing component.

The present invention features a portable pathogen analysis system for detecting a microorganism in a liquid sample. In certain embodiments, the system comprises a microfluidic disc integrated into a portable analysis device. In certain embodiments, the microfluidic disc comprises an inlet fluidly connected to an inlet chamber, wherein a concentrated sample can be introduced to the inlet chamber via the inlet; a clarification chamber fluidly connected to the inlet chamber via a passive valve; a waste chamber fluidly connected to the clarification chamber; a reagent chamber for holding nucleic acid amplification reagents; a mixing chamber fluidly connected to the reagent chamber via a siphon valve and fluidly connected to the clarification chamber via a siphon valve, the mixing chamber mixes the nucleic acid amplification reagents and the sample from the clarification chamber; a reaction chamber fluidly connected to the mixing chamber; and an oil chamber for holding oil, wherein oil is introduced to fluid moving from the mixing chamber to the reaction chamber to form water-in-oil droplets, wherein the water-in-oil droplets allow for nucleic acid amplification in the reaction chamber. In certain embodiments, the portable analysis device functions to rotate the microfluidic device; to heat and cool the microfluidic device so as to effectively achieve amplification of nucleic acid in the water-in-oil droplets in the reaction chamber; and to analyze signals from the water-in-oil droplets to determine a concentration of the target nucleic acid in the sample.

In certain embodiments, the nucleic acid amplification reagents comprise at least primers specific for a target nucleic acid associated with the microorganism.

In certain embodiments, detecting the target nucleic acid associated with the microorganism is indicative of the presence of the microorganism in the liquid sample.

In certain embodiments, the microfluidic disc is disposable. In certain embodiments, flow of the concentrate and reagents on the microfluidic disc is controlled by rotation speeds and passive valves. In some embodiments, cell lysis is achieved in the inlet chamber. In certain embodiments, cell lysis is achieved via mechanical bead-beating induced by magnetic actuation at a first rotational speed. In some embodiments, the first rotational speed is 200 rpm. In some embodiments, a second rotational speed can break the passive valve to allow fluid from the inlet chamber to the clarification chamber. In some embodiments, the second rotational speed is 3000 rpm. The present invention is not limited to the aforementioned rotational speeds.

In some embodiments, the system can detect the microorganism within 2 hours after a sample has been inserted into the inlet chamber. In some embodiments, the nucleic acid amplification reagents are manually loaded into the reagent chamber prior to use. In some embodiments, the nucleic acid amplification reagents are lyophilized and present in the reagent chamber prior to use. In certain embodiments, nucleic acid amplification is achieved via loop-mediated isothermal amplification (LAMP). In some embodiments, the portable analysis device can rotate the microfluidic device at varying speeds. In some embodiments, the portable analysis device comprises a display operatively connected to a computer. In some embodiments, heating and cooling the microfluidic device is achieved by infrared lamps and by disc rotation in the portable analysis device, respectively.

In some embodiments, the portable analysis device comprises a light source for dye excitation for fluorescence measurements. In some embodiments, the light source is a blue LED light source. In some embodiments, the portable analysis device comprises a camera for taking digital images of fluorescence of the oil-in-water droplets. In some embodiments, the portable analysis device processes the digital images with software to calculate a concentration of the microorganism in the sample with Poisson distribution analysis.

In some embodiments, the system further comprises a concentration tube, the concentration tube comprises a tube for holding a liquid; superabsorbent polymer (SAP) beads; and a filter positioned a distance above a bottom end of the tube to exclude the beads from the bottom end of the tube.

In some embodiments, the tube is a 15 mL tube. In some embodiments, the tube is a 50 mL tube. In some embodiments, the water-in-oil droplets provide individual nucleic acid amplification reactions. In some embodiments, some of the water-in-oil droplets contain the target nucleic acid, and some of the water-in-oil droplets do not contain the target nucleic acid. The present invention is not limited to the aforementioned tube sizes.

The present invention also features a method of detecting a microorganism in a liquid sample. In some embodiments, the method comprises adding a volume of the liquid sample to a concentration tube of the preset invention (e.g., the concentration tube comprises a tube for holding a liquid; superabsorbent polymer (SAP) beads; and a filter positioned a distance above a bottom end of the tube to exclude the beads from the bottom end of the tube); incubating the concentration tube for a first length of time; and centrifuging the concentration tube by hand for a second length of time, wherein the SAP beads remain above the filter and concentrate collects in the bottom end of the tube, wherein at least a portion of the microorganisms remain in the concentrate. In certain embodiments, the method further comprises introducing at least a portion of the concentrate to a system of the present invention, e.g., as described above. In certain embodiments, the portable analysis device comprises a light source for exciting a fluorescent dye in the water-in-oil droplets, a digital camera for obtaining a digital image of the fluorescent dye; and a microprocessor with software for processing the digital image of the fluorescent dye in the water-in-oil droplets.

The method may further comprise lysing cells in the inlet chamber via mechanical bead-beating induced by magnetic actuation of the microfluidic device at a first rotation speed; increasing rotational speed of the microfluidic device to a second rotational speed to break the passive valve, wherein cell debris is attenuated in the clarification chamber and DNA is left in supernatant; combining and rotating at a third rotation speed supernatant from the clarification chamber and nucleic acid amplification reagents from the reagent chamber moving in the mixing chamber via the siphon valves; forming water-in-oil droplets from fluid moving from the mixing chamber to the reaction chamber via centrifugal emulsification; subjecting the water-in-oil droplets to nucleic acid amplification via heating and cooling cycles of the reaction chamber; exciting the dye in the water-in-oil droplets via the light source; obtaining a digital image of the water-in-oil droplets with the digital camera; and processes the digital image with the software to calculate a concentration of the microorganism in the sample with Poisson distribution analysis.

In certain embodiments, detection of the target nucleic acid associated with the microorganism is indicative of the presence of the microorganism in the liquid sample.

In some embodiments, the concentrate has a volume that is no more than 20% of the volume of the liquid sample added to the concentration tube. In some embodiments, the concentrate has a volume that is no more than 15% of the volume of the liquid sample added to the concentration tube. In some embodiments, the concentrate has a volume that is no more than from 5 to 15% of the volume of the liquid sample added to the concentration tube.

In some embodiments, the portion of the microorganisms that remain in the concentrate is at least 60% of that in the liquid sample before the liquid sample is added to the concentration tube. In some embodiments, the portion of the microorganisms that remain in the concentrate is at least 80% of that in the liquid sample before the liquid sample is added to the concentration tube.

In some embodiments, the first length of time is from 1 to 10 minutes. In some embodiments, the first length of time is from 4 to 8 minutes. In some embodiments, the second length of time is from 1 to 2 minutes. In some embodiments, incubating the concentration tube for a first length of time includes gentle rocking or waving of the concentration tube intermittently. In some embodiments, the microfluidic disc is disposable. In some embodiments, the rotational speed is 200 rpm. In some embodiments, the second rotational speed is 3000 rpm. In some embodiments, the third rotational speed is 400 rpm. The present invention is not limited to the aforementioned rotational speeds. The present invention is not limited to the aforementioned time frames.

In certain embodiments, the method can detect the microorganism within 2 hours after a sample has been added to the concentration tube. In certain embodiments, the nucleic acid amplification reagents are manually loaded into the reagent chamber prior to use. In certain embodiments, the nucleic acid amplification reagents are lyophilized and present in the reagent chamber prior to use.

In certain embodiments, nucleic acid amplification is achieved via loop-mediated isothermal amplification (LAMP). In certain embodiments, the portable analysis device can rotate the microfluidic device at varying speeds. In certain embodiments, the portable analysis device comprises a display operatively connected to a computer. In certain embodiments, heating and cooling the microfluidic device for nucleic acid amplification is achieved by infrared lamps and disc rotation in the portable analysis device, respectively.

In some embodiments, the light source is a blue LED light source. In some embodiments, the water-in-oil droplets provide individual nucleic acid amplification reactions. In some embodiments, some of the water-in-oil droplets contain the target nucleic acid, and some of the water-in-oil droplets do not contain the target nucleic acid.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

This patent application contains at least one drawing executed in color. Copies of this patent or patent application publication with color drawing(s) will be provided by the Office upon request and payment of the necessary fee.

The features and advantages of the present invention will become apparent from a consideration of the following detailed description presented in connection with the accompanying drawings in which.

TERMS

Figure 1:
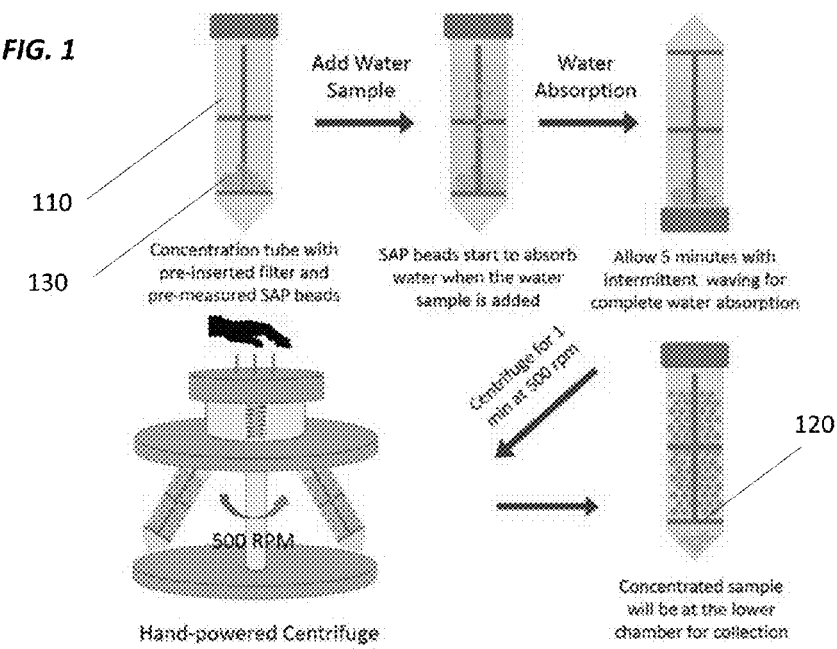
FIG. 1 shows a schematic view of the concentration tube of the system of present invention, wherein water is concentrated using superabsorbent polymer beads in a tube and a hand-powered centrifuge.

Unless otherwise explained, all technical and scientific terms used herein have the same meaning as commonly understood by one of ordinary skill in the art to which a disclosed invention belongs. The singular terms "a," "an," and "the" include plural referents unless context clearly indicates otherwise. Similarly, the word "or" is intended to include "and" unless the context clearly indicates otherwise. "Comprising" means "including." Hence "comprising A or B" means "including A" or "including B" or "including A and B."

Suitable methods and materials for the practice and/or testing of embodiments of the disclosure are described below. Such methods and materials are illustrative only and are not intended to be limiting. Other methods and materials similar or equivalent to those described herein can be used. For example, conventional methods well known in the art to which the disclosure pertains are described in various general and more specific references, including, for example, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999, the disclosures of which are incorporated in their entirety herein by reference.

All publications, patent applications, patents, and other references mentioned herein are incorporated by reference in their entirety.

Although methods and materials similar or equivalent to those described herein can be used to practice or test the disclosed technology, suitable methods and materials are described below. The materials, methods, and examples are illustrative only and not intended to be limiting.

In order to facilitate review of the various embodiments of the disclosure, the following explanations of specific terms are provided:

Probes and primers: A probe comprises an isolated nucleic acid attached to a detectable label or reporter molecule. Primers are short nucleic acids, and can be DNA oligonucleotides 15 nucleotides or more in length, for example. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, for example, by the polymerase chain reaction (PCR) or other nucleic-acid amplification methods known in the art such as LAMP. One of skill in the art will appreciate that the specificity of a particular probe or primer increases with its length. Thus, for example, a primer comprising 20 consecutive nucleotides will anneal to a target with a higher specificity than a corresponding primer of only 15 nucleotides.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2'-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

Pathogen: A biological agent that causes disease or illness to its host. Pathogens include, for example, bacteria, viruses, fungi, protozoa and parasites. Pathogens are also referred to as infectious agents.

Examples of pathogenic viruses include those in the following virus families: Retroviridae (for example, human immunodeficiency virus (HIV); human T-cell leukemia viruses (HTLV); Picornaviridae (for example, polio virus, hepatitis A virus; hepatitis C virus; enteroviruses, human coxsackie viruses, rhinoviruses, echoviruses; foot-and-mouth disease virus); Calciviridae (such as strains that cause gastroenteritis); Togaviridae (for example, equine encephalitis viruses, rubella viruses); Flaviridae (for example, dengue viruses; yellow fever viruses; West Nile virus; St. Louis encephalitis virus; Japanese encephalitis virus; and other encephalitis viruses); Coronaviridae (for example, coronaviruses; severe acute respiratory syndrome (SARS) virus; Rhabdoviridae (for example, vesicular stomatitis viruses, rabies viruses); Filoviridae (for example, Ebola viruses); Paramyxoviridae (for example, parainfluenza viruses, mumps virus, measles virus, respiratory syncytial virus (RSV)); Orthomyxoviridae (for example, influenza viruses); Bunyaviridae (for example, Hantaan viruses; Sin Nombre virus, Rift Valley fever virus; bunya viruses, phleboviruses and Nairo viruses); Arena viridae (hemorrhagic fever viruses; Machupo virus; Junin virus); Reoviridae (e.g., reo viruses, orbiviurses and rotaviruses); Birnaviridae; Hepadnaviridae (Hepatitis B virus); Parvoviridae (parvoviruses); Papovaviridae (papilloma viruses, polyoma viruses; B K-virus); Adenoviridae (most adenoviruses); Herpesviridae (herpes simplex virus (HSV)-1 and HSV-2; cytomegalovirus (CMV); Epstein-Barr virus (EBV); varicella zoster virus (VZV); and other herpes viruses, including HSV-6); Poxviridae (variola viruses, vaccinia viruses, pox viruses); and Iridoviridae (such as African swine fever virus); Filoviridae (for example, Ebola virus; Marburg virus); Caliciviridae (for example, Norwalk viruses) and unclassified viruses (for example, the etiological agents of Spongiform encephalopathies, the agent of delta hepatitis (thought to be a defective satellite of hepatitis B virus); and astroviruses).

Examples of fungal pathogens include, but are not limited to: *Cryptococcus neoformans, Histoplasma capsulatum, Coccidioides immitis, Blastomyces dermatitidis, Chlamydia trachomatis, Candida albicans.*

Examples of bacterial pathogens include, but are not limited to: *Helicobacter pylon, Borelia burgdorferi, Legionella pneumophilia, Mycobacteria* species (such as *M. tuberculosis, M. avium, M. intracellular, M. kansaii, M. gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic species), *Streptococcus pneumoniae,* pathogenic *Campylobacter* species, *Enterococcus* species, *Haemophilus influenzae, Bacillus anthracis, Corynebacterium diphtherias, corynebacterium* species, *Erysipelothrix rhusiopathiae, Clostridium perfringers, Clostridium tetani, Enterobacter aerogenes, Klebsiella pneumoniae, Pastumlla multocida, Bacteroides* species, *Fusobacterium nucleatum, Streptobacillus rnoniliformis, Treponema pallidiurn, Treponema pertenue, Leptospira,* and *Actinomyces israelii.*

Other pathogens (such as protists) include: *Plasmodium falciparum* and *Toxoplasma gondii.*

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

DETAILED DESCRIPTION OF THE INVENTION

The present invention features a portable pathogen analysis system (PPAS) for assessing water quality by detecting pathogens. The stand-alone system of the present invention facilitates microbial water quality analysis at the point-of-sample collection, particularly in a resource-limited setting.

The use of the system only requires one step wherein the sample is loaded into the system. The final quantitative results can be acquired within a few hours, e.g., 1-2 hours, 1-3 hours, 2-4 hours, etc.

Concentration Tube

Referring to FIG. 1, the system of the present invention comprises a concentration tube (110) designed for concentrating the pathogen without using electricity. The concentration tube may be any appropriate size, e.g., a 10 mL tube, a 25 mL tube, a 50 mL tube. etc. The concentration tube (110) comprises a filter (120) and superabsorbent polymer (SAP) beads (130). In certain embodiments, the SAP beads (130) are positioned above the filter (120), e.g., as shown in FIG. 1.

Superabsorbent polymers are well known to one of ordinary skill in the art. In certain embodiments, the SAP beads (130) are constructed from material comprising sodium polyacrylate, polyacrylamide copolymer, ethylene maleic anhydride copolymer, etc. SAP beads may be synthesized using a milli-fluidic T-junction system as described in Xie, Xing, et al. (*Scientific reports* 6 (2016): 20516).

In certain embodiments, the concentration tube can concentrate 35 mL of sample to 3-4 mL of concentrated sample, e.g., the concentration tube can concentrate a sample to 8-11% of its initial volume. In certain embodiments, the concentration tube can concentrate a sample to 1% of its initial volume. In certain embodiments, the concentration tube can concentrate a sample to 2% of its initial volume. In certain embodiments, the concentration tube can concentrate a sample to 3% of its initial volume. In certain embodiments, the concentration tube can concentrate a sample to 4% of its initial volume. In certain embodiments, the concentration tube can concentrate a sample to 5% of its initial volume. In certain embodiments, the concentration tube can concentrate a sample to 6% of its initial volume. In certain embodiments, the concentration tube can concentrate a sample to 7% of its initial volume. In certain embodiments, the concentration tube can concentrate a sample to 8% of its initial volume. In certain embodiments, the concentration tube can concentrate a sample to 9% of its initial volume. In certain embodiments, the concentration tube can concentrate a sample to 10% of its initial volume. In certain embodiments, the concentration tube can concentrate a sample to 11% of its initial volume. In certain embodiments, the concentration tube can concentrate a sample to 12% of its initial volume. In certain embodiments, the concentration tube can concentrate a sample to 13% of its initial volume. In certain embodiments, the concentration tube can concentrate a sample to 14% of its initial volume. In certain embodiments, the concentration tube can concentrate a sample to 15% of its initial volume. In certain embodiments, the concentration tube can concentrate a sample from 15 to 20% of its initial volume. In certain embodiments, the concentration tube can concentrate a sample from 20 to 25% of its initial volume. In certain embodiments, the concentration tube can concentrate a sample from 25 to 50% of its initial volume.

The concentration efficiency of the concentration tube can be determined using a control sample with a bacterium or microbe of interest (e.g., pure cultured *E. coli* (ATCC 10798)), The concentration of bacterium before and after processing with the concentration tube can be counted by fluorescence microscopy (e.g., with SYBR-Green I staining). The present invention is not limited to the aforementioned materials and methods for analyzing efficiency of the concentration tube or methods.

In some embodiments, the bacterial recovery rate is from 50-60%. In some embodiments, the bacterial recovery rate is from 60-70%. In some embodiments, the bacterial recovery rate is from 70-80%. In some embodiments, the bacterial recovery rate is from 80-90%. In some embodiments, the bacterial recovery rate is from 90-99%.

A liquid (e.g., sewage water) sample is added to the concentration tube (110). The sample mixes with the SAP beads (130), which start to absorb water when the sample is added. The concentration tube (110) with the sample is allowed to incubate for a certain length of time, e.g., 2 minutes, 3 minutes, 4 minutes, 5 minutes, 6 minutes, 7 minutes, 8 minutes, 9 minutes, 10 minutes, more than 10 minutes, etc. In certain embodiments, during the incubation time, the concentration tube (110) is rocked, moved, waved, etc. intermittently to help mixing and/or water absorption. Next, the concentration tube (110) is centrifuged using a hand-powered centrifuge (140) or other appropriate centrifuge system. Due to size exclusion and charge repulsion, the SAP beads (130) only absorb water via osmosis, while the target microorganisms in the sample (if present) are excluded and remain in the concentrate after low-speed hand-powered centrifugation (see FIG. 1). In certain embodiments, the concentration tube (110) is centrifuged for 1 minute in a hand-powered centrifuge. The present invention is not limited to 1 minute and includes any appropriate length of time to concentrate the sample.

Processing Component

Figure 2:
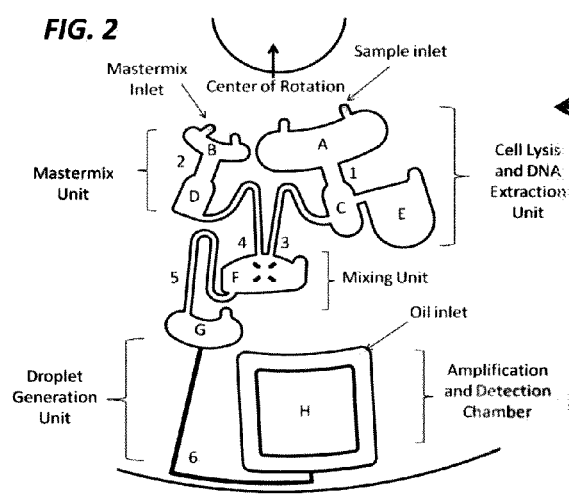
FIG. 2 shows a schematic view of a microfluidic disc of the processing component of the system of the present invention.
Figure 3:
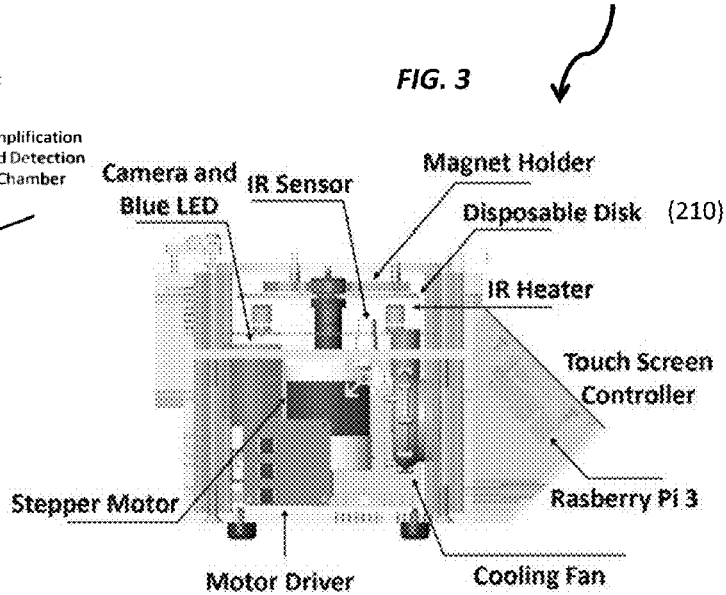
FIG. 3 shows a schematic view of the portable analysis device of the system of the present invention.

After the sample is concentrated using the concentration tube, the concentrated sample is processed using the processing component. Referring to FIG. 2 and FIG. 3, the processing component comprises a microfluidic disc (210) (e.g., a disposable microfluidic device) integrated into a portable analysis device (310), e.g., a rotation-based thermal cycler. The processing component features four steps: cell lysis, reagent-mixing, droplet generation and digital nucleic acid amplification. Digital nucleic acid amplification works by partitioning one bulk reaction into 20,000+ individual amplification reactions (water-in-oil droplets). Some of the reactions contain the target DNA template (positive), while others do not (negative). At the end of the reaction, the positive and negative reactions are determined by their fluorescent signal, from which the original sample DNA concentration is estimated by modeling as Poisson distribution.

Microfluidic Disc: The microfluidic disc (210) comprises three layers: a top disc (e.g., polycarbonate disc) with inlets and venting holes; a middle biocompatible adhesive membrane layer consisting some of the channels; and the bottom layer with chambers and remaining channels (e.g., computer numerical control (CNC) milled polycarbonate layer). The flow of sample and reagents on the microfluidic disc (210) is controlled by different rotation speeds and various passive valves. In some embodiments, the disc is constructed with a computer numerical control (CNC) machine or with polydimethylsiloxane (PDMS) by standard photolithographic methods. In some embodiments, hot embossing or injection molding methods may be used for disc production. In some embodiments, 3-D printing may be used to create a section of the disc.

Referring to FIG. 2, the sample is added to an inlet chamber (Part A) via the sample inlet. In the inlet chamber (Part A), cell lysis is achieved via mechanical bead-beating induced by magnetic actuation at a rotation speed, e.g., a rotation speed of about 200 rpm. Increasing the rotational speed to 3000 rpm breaks the hydrophobic passive valve (Part 1). Cell lysis containing target DNA is flowing in the clarification chamber (Part C) and overflowing waste chamber (Part E). The rotation force also pellets the cell debris to bottom of the chamber C & E, while the target DNA is left in the supernatant and is allowed to enter hydrophilic siphon valve (Part 3). The clarification chamber is designed as a volume metering chamber (Part C), together with hydrophilic siphon valve (Part 3). A fixed volume of supernatant (e.g., 5 µL) from the clarification chamber (Part C) can enter reagent mixing chamber. A mirror image is used for reagent chamber (Part B, Part D) and siphon valve (Part 4). The reagent chamber is prefilled with reagents for amplification (e.g., amplification Mastermix, e.g., WarmStart Colorimetric LAMP 2× Master Mix (e.g., 20 µL)). The next rotation, e.g., at 400 rpm, forces reagent from the reagent chamber (Part D) and DNA supernatant from clarification chamber (Part C) simultaneously entering into the mixing chamber (Part F). In some embodiments, an X design in the center of the chamber is used to direct the fluid flow pattern and mix it as it exits the siphon. The well-mixed bulk reaction fluid is stored in chamber G. By using a modified centrifugal step emulsification design described by Schuler et al. (Lab on a Chip 16.1 (2016): 208-216), water-in-oil droplets (e.g., 100 to 150 µm in diameter) are generated using rotation, e.g., speeds of 1000 to 1500 rpm. The dimension of the reaction channel (Part 6) controls the size of the water-in-oil droplets. Part H is the droplet chamber as well as the reaction chamber. The amplification and positive/negative droplet detection are automatically controlled by the system.

In some embodiments, the reagents and samples are manually loaded into the reaction chambers. In some embodiments, lyophilized reagents are pre-loaded, and users only need to load the sample in the sample inlet, e.g., with a syringe.

Portable Analysis Device: The microfluidic disc (e.g., disposable microfluidic disc) is integrated into the portable analysis device, which provides the rotation of the microfluidic disc at varying speeds, controls temperature (heating and cooling) for nucleic acid amplification, and performs the analysis. The integrated nature of the microfluidic disc and portable analysis device allows the DNA extraction, droplet formation, and nucleic acid amplification reactions to be seamlessly connected without the need to transfer the sample from one vial to another as would be done in a typical laboratory.

The portable analysis device, as shown in FIG. 3, comprises a display such as a touchscreen controller operatively connected to a computer (e.g., a Raspberry Pi 3). The on-disc temperature control is implemented by using five infrared lamps for heating and disc rotation for air-cooling. A light source, e.g., a blue LED (470 nm) light source, is employed for dye excitation for droplets fluorescence measurements. An in situ camera takes digital images. The image is processed immediately with pre-installed commercial software to determine the target microbial concentrations based on a Poisson distribution analysis (e.g., software from ImageJ, which is well known to one of ordinary skill in the art).

A sample protocol of detecting *Enterococcus* in sewage water on disc is as follows: 1) inject sample into sample port; 2) cell lysis by bead-beating 200 rpm-6 min; 3) DNA clarification 3000 rpm-10 s; 4) siphon priming, reagent release, reaction mixing, 0rpm-20 s, 500 rpm-4 s, 2000 rpm-20 s, 0 rpm-20 s, 500 rpm-30 s; 5) droplet generation 1000 rpm-45 s, 6) amplification 65° C. 30 rpm-30 min; 7) detection. The protocol is programed in the control system. The completion of the protocol is achieved by a push of start button. In some embodiments, a commercial amplification reaction mix is used, e.g., WarmStart 2× LAMP Mastermix for amplification and Novec HEFE 7500 oil contained 5 wt % Fluor-surfactant is used for droplet generation. The LAMP reagent and oil may be pre-filled onto the disc in chamber (Part B, Part H). The present invention is not limited to the aforementioned compositions or methods, e.g., other rotational speeds or reagents may be considered, etc.

The present invention is not limited to any particular nucleic acid amplification system. For example, in some embodiments, nucleic acid amplification is accomplished using loop-mediated isothermal amplification (LAMP). In some embodiments, polymerase chain reaction may be considered.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A portable pathogen analysis system for detecting a microorganism in a liquid sample, said system comprising:
    a. a microfluidic disc comprising:
        i. an inlet fluidly connected to an inlet chamber, wherein a concentrated sample is introduced to the inlet chamber via the inlet;
        ii. a clarification chamber fluidly connected to the inlet chamber via a passive valve;
        iii. a waste chamber fluidly connected to the clarification chamber;
        iv. a reagent chamber for holding nucleic acid amplification reagents, the nucleic acid amplification reagents comprise at least primers specific for a target nucleic acid associated with the microorganism;
        v. a mixing chamber fluidly connected to the reagent chamber via a siphon valve and fluidly connected to the clarification chamber via a siphon valve, the mixing chamber mixes the nucleic acid amplification reagents and the sample from the clarification chamber;
        vi. a reaction chamber fluidly connected to the mixing chamber; and
        vii. an oil chamber for holding oil, wherein oil is introduced to fluid moving from the mixing chamber to the reaction chamber to form water-in-oil droplets, wherein the water-in-oil droplets allow for nucleic acid amplification in the reaction chamber;
    b. a portable analysis device in which the microfluidic disc is integrated, the portable analysis device functions to heat and cool the microfluidic disc so as to effectively achieve nucleic acid amplification of nucleic acid in the water-in-oil droplets in the reaction chamber; and to analyze signals from the water-in-oil droplets to determine a concentration of the target nucleic acid in the sample; and
    c. a stepper motor operatively coupled to the microfluidic disc, wherein the stepper motor functions to rotate the microfluidic disc;
    wherein detecting the target nucleic acid associated with the microorganism is indicative of the presence of the microorganism in the liquid sample.

2. The system of claim 1, wherein the microfluidic disc is disposable.

3. The system of claim 1, wherein flow of the concentrate and reagents on the microfluidic disc is controlled by rotation speeds and passive valves.

4. The system of claim 1, wherein cell lysis is achieved in the inlet chamber.

5. The system of claim 4, wherein cell lysis is achieved via mechanical bead-beating induced by magnetic actuation at a first rotational speed.

6. The system of claim 5, wherein a second rotational speed can break the passive valve to allow fluid from the inlet chamber to the clarification chamber.

7. The system of claim 1, wherein nucleic acid amplification is achieved via loop-mediated isothermal amplification (LAMP).

8. The system of claim 1, wherein the portable analysis device can rotate the microfluidic disc at varying speeds.

9. The system of claim 1, wherein the portable analysis device comprises a display operatively connected to a computer.

10. The system of claim 1, wherein the portable analysis device comprises a light source for dye excitation for fluorescence measurements.

11. The system of claim 10, wherein the portable analysis device comprises a camera for taking digital images of fluorescence of the oil-in-water droplets.

12. The system of claim 11, wherein the portable analysis device processes the digital images with software to calculate a concentration of the microorganism in the sample with Poisson distribution analysis.

13. The system of claim 1, further comprising a concentration tube, the concentration tube comprises a tube for holding a liquid; superabsorbent polymer (SAP) beads; and a filter positioned a distance above a bottom end of the tube to exclude the beads from the bottom end of the tube.

14. A method of detecting a microorganism in a liquid sample, said method comprising:
   a. adding a volume of the liquid sample to a concentration tube, the concentration tube comprises a tube for holding a liquid; superabsorbent polymer (SAP) beads; and a filter positioned a distance above a bottom end of the tube to exclude the beads from the bottom end of the tube;
   b. incubating the concentration tube for a first length of time;
   c. centrifuging the concentration tube by hand for a second length of time, wherein the SAP beads remain above the filter and concentrate collects in the bottom end of the tube, wherein at least a portion of the microorganisms remain in the concentrate;
   d. introducing at least a portion of the concentrate to a system comprising:
      i. a microfluidic disc comprising:
         1. an inlet fluidly connected to an inlet chamber, wherein the at least a portion of the concentrate is introduced to the inlet chamber via the inlet;
         2. a clarification chamber fluidly connected to the inlet chamber via a passive valve;
         3. a waste chamber fluidly connected to the clarification chamber;
         4. a reagent chamber for holding nucleic acid amplification reagents, the nucleic acid amplification reagents comprise at least primers specific for a target nucleic acid associated with the microorganism;
         5. a mixing chamber fluidly connected to the reagent chamber via a siphon valve and fluidly connected to the clarification chamber via a siphon valve, the mixing chamber mixes the nucleic acid amplification reagents and the sample from the clarification chamber;
         6. a reaction chamber fluidly connected to the mixing chamber; and
         7. an oil chamber for holding oil, wherein oil is introduced to fluid moving from the mixing chamber to the reaction chamber to form water-in-oil droplets, wherein the water-in-oil droplets allow for nucleic acid amplification in the reaction chamber;
      ii. a portable analysis device in which the microfluidic disc is integrated, the portable analysis device functions to heat and cool the microfluidic disc so as to effectively achieve nucleic acid amplification of nucleic acid in the water-in-oil droplets in the reaction chamber; and to analyze signals from the water-in-oil droplets to determine a concentration of the target nucleic acid in the sample, the portable analysis device comprises a light source for exciting a fluorescent dye in the water-in-oil droplets, a digital camera for obtaining a digital image of the fluorescent dye; and a microprocessor with software for processing the digital image of the fluorescent dye in the water-in-oil droplets; and
      iii. a stepper motor operatively coupled to the microfluidic disc, wherein the stepper motor functions to rotate the microfluidic disc;
   e. lysing cells in the inlet chamber via mechanical bead-beating induced by magnetic actuation of the microfluidic disc at a first rotation speed;
   f. increasing rotational speed of the microfluidic disc to a second rotational speed to break the passive valve, wherein cell debris is attenuated in the clarification chamber and DNA is left in supernatant;
   g. combining and rotating at a third rotation speed supernatant from the clarification chamber and nucleic acid amplification reagents from the reagent chamber in the mixing chamber via the siphon valves;
   h. forming water-in-oil droplets from fluid moving from the mixing chamber to the reaction chamber via centrifugal emulsification;
   i. subjecting the water-in-oil droplets to nucleic acid amplification via heating and cooling cycles of the reaction chamber;
   j. exciting the dye in the water-in-oil droplets via the light source;
   k. obtaining a digital image of the water-in-oil droplets with the digital camera; and
   l. processes the digital image with the software to calculate a concentration of the microorganism in the sample with Poisson distribution analysis;
   wherein detection of the target nucleic acid associated with the microorganism is indicative of the presence of the microorganism in the liquid sample.

15. The method of claim 14, wherein the concentrate has a volume that is no more than from 5 to 15% of the volume of the liquid sample added to the concentration tube.

16. The method of claim 14, wherein the portion of the microorganisms that remain in the concentrate is at least 60% of that in the liquid sample before the liquid sample is added to the concentration tube.

17. The method of claim 14, wherein the method can detect the microorganism within 2 hours after a sample has been added to the concentration tube.

18. The method of claim 14, wherein nucleic acid amplification is achieved via loop-mediated isothermal amplification (LAMP).

19. The method of claim 14, wherein the portable analysis device comprises a display operatively connected to a computer.

20. The method of claim 14, wherein heating and cooling the microfluidic disc for nucleic acid amplification is achieved by infrared lamps and disc rotation in the portable analysis device, respectively.

* * * * *